United States Patent
Mann et al.

(10) Patent No.: US 6,967,249 B2
(45) Date of Patent: Nov. 22, 2005

(54) PHOTOCHROMIC 3H-NAPHTHO[2,1-B]-PYRAN COMPOUNDS AND PHOTOCHROMIC ARTICLES PRODUCED THEREWITH

(75) Inventors: Claudia Mann, Munich (DE); Manfred Melzig, Wessling (DE); Udo Weigand, Munich (DE)

(73) Assignee: Rodenstock GmbH, Munich (DE)

( * ) Notice: Subject to any disclaimer, the term of this patent is extended or adjusted under 35 U.S.C. 154(b) by 59 days.

(21) Appl. No.: 10/883,647

(22) Filed: Jul. 2, 2004

(65) Prior Publication Data

US 2004/0267013 A1 Dec. 30, 2004

Related U.S. Application Data

(63) Continuation of application No. PCT/EP02/14688, filed on Dec. 20, 2002.

(30) Foreign Application Priority Data

Jan. 3, 2002 (DE) .......................... 102 00 040

(51) Int. Cl.$^7$ .......................... C07D 311/92; C03C 4/00; C03C 3/32

(52) U.S. Cl. .......................... 544/60; 544/106; 549/389; 501/13; 501/40

(58) Field of Search .................... 544/60, 106; 549/389; 501/13, 40

(56) References Cited

U.S. PATENT DOCUMENTS

| 5,238,981 A | 8/1993 | Knowles |
| 5,990,305 A | 11/1999 | Melzig et al. |

FOREIGN PATENT DOCUMENTS

| EP | 945451 A | 9/1999 |
| JP | 08 157467 A | 10/1996 |
| JP | 08 176139 A | 11/1996 |
| WO | 98 45281 A | 10/1998 |
| WO | 01 12619 A | 2/2001 |

*Primary Examiner*—Taofiq Solola
(74) *Attorney, Agent, or Firm*—Crowell & Moring LLP

(57) ABSTRACT

Specific photochromic 3H-naphtho[2,1-b]-pyran compounds useful with various types of synthetic resin materials to form photochromic articles, especially ophthalmic lenses, and photochromic articles formed with such compounds. The compounds of the invention have especially long-wave absorption maxima in the open form thereof and enable violet to blue tints to be obtained when used in photochromic articles.

10 Claims, 1 Drawing Sheet

PHOTOCHROMIC 3H-NAPHTHO[2,1-B]-PYRAN COMPOUNDS AND PHOTOCHROMIC ARTICLES PRODUCED THEREWITH

CROSS REFERENCE TO RELATED APPLICATIONS

This application is a continuation of international patent application No. PCT/EP02/14688, filed Dec. 20, 2002, designating the United States of America, and published in German as WO 03/055862, the entire disclosure of which is incorporated herein by reference.

BACKGROUND OF THE INVENTION

The present invention relates to specific photochromic 3H-naphtho[2,1-b]-pyran compounds and to their use in plastics of all types, especially for ophthalmic purposes. In particular, the present invention relates to photochromic compounds, which are derived from 3H-naphtho[2,1-b]-pyrans and which, in their open form, have long wavelength absorption maxima, as a result of which violet to blue color shades can be achieved, especially when used in eyeglasses.

Various classes of dyes are known, which reversibly change their color when they are irradiated with light of particular wavelengths, especially with sunlight, because such dye molecules, when supplied with energy in the form of light, are transformed into an excited, colored state. When the energy is no longer supplied, then they leave this exited state once again and return to their normal, colorless or hardly colored state. These photochromic dyes include, for example, the naphthopyrans, which have already been described with various substituents in the prior art.

Pyrans, especially naphthopyrans and larger ring systems derived from these, are photochromic compounds, which have been the object of intensive investigations up to the present time. Although a patent was filed for the first time in 1966 (U.S. Pat. No. 3,567,605), compounds which appear to be suitable for use in eyeglasses were not developed until the 1990s.

The photochromic dyes, known in the prior art, on the one hand, frequently have inadequate absorption at long wavelengths both in the excited state and in the unexcited state. This leads to problems, even in combinations with other photochromic dyes. On the other hand, there is frequently also an excessively high temperature sensitivity with respect to the darkening and, at the same time, the brightening is too slow. Furthermore, the dyes, available in the prior art frequently have an inadequate service life. Consequently, sunglasses made with such dyes are do not have sufficient stability. The instability of such sunglasses quickly becomes noticeable due to a rapid decrease in performance and/or due to severe yellowing.

3H-naphthopyrans derived from 2-naphthols and their higher analogue compounds derived from 3H-naphthopyrans by annelation, constitute a group of photochromic dyes in which the longest wave absorption maximum of the excited form lies predominantly in the spectral range from 420 nm to 500 nm and accordingly imparts a yellow, orange or red color sensation (see U.S. Pat. Nos, 5,869,658 and 6,022,495). However, for neutral darkening photochromic glasses, powerful, violet to blue photochromic dyes are required. The violet to blue photochromic dyes presently available in the art, usually originate from the class of spiroxazines, fulgides or 2H-naphtho[1,2-b]pyrans. However, spiroxazine dyes are usually not satisfactory with respect to their high-temperature performance, while the service life of fulgide dyes and the rate of brightening of 2H-naphtho[1,2-b]pyrans are not entirely satisfactory for use in sunglasses.

The introduction of electron-shifting substituents in aryl groups in the ortho position to the pyran oxygen, for example, as described in WO 98/45281, WO 01/12619 and EP 0 945451 A1, leads to red or red violet darkening 3H-naphtho[2,1-b]pyrans. WO 01/12619 discloses compounds having one geminal aryl group which has a p-amino-substituted group and another aryl group which has an alkoxy or thioalkoxy substituent group in the meta or para position, this substitution pattern having a positive effect on the brightening rate. In the WO 98/45281, red hyperchromic compounds are described, which additionally contain an amine function predominantly in the 6 position of the 3H-naphtho[2,1-b]-pyran unit. Compounds with not pronounced basic amino groups are described in the EP 0 945 451 A1. In the excited state, these compounds have a pink to violet color, as well as an attractive service life. Appropriate substitution, especially the introduction of alkoxy groups, in the 8 position of the 3H-naphtho[2,1-b]-pyran unit brings about a bathochromic shift in the longest wavelength absorption maximum, as described in U.S. Pat. No. 5,238,981. Furthermore, compounds with dialkylamino groups in the 8 position are also disclosed. The use of nitrogen-containing heterocyclic groups as substituents in the 8 position of the 3H-naphtho[2,1-b]-pyran unit is mentioned in U.S. Pat. No. 5,990,305, as a result of which, in contrast to open-chain amino groups, an improved service life is achieved. This is also attained with substituents which contain the so-called HALS (hindered amine light stabilizer) structure elements.

SUMMARY OF THE INVENTION

Accordingly, it is an object of the present invention to provide new photochromic dyes, which have improved properties in comparison to compounds described in the art.

Another object of the invention is to provide photochromic dyes which, in comparison to compounds of the prior art, absorb at longer wavelengths in the excited state.

A further object is to provide photochromic compounds which have good kinetic and service life properties, i.e., rapid brightening rates and good performance in the service life test.

These and other objects are achieved in accordance with the present invention by providing a photochromic 3H-naphtho[2,1-b]-pyran compound as described and claimed hereinafter.

In another aspect, the objects of the invention are achieved by providing a photochromic article comprising a synthetic resin body and an effective photochromic amount of at least one 3H-naphtho[2,1-b]-pyran compound according to the invention.

In particular, photochromic 3H-naphtho[2,1-b]-pyran compounds corresponding to the formula (I)

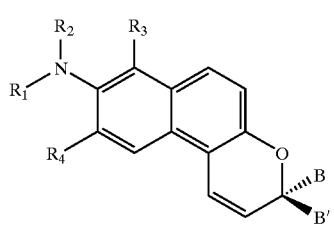

(I)

are provided, in which $R_1$ and $R_2$ each independently represent a substituent selected from the α group consisting of a linear or branched $(C_1-C_6)$ alkyl group, a $(C_3-C_7)$ cycloalkyl group and an unsubstituted, monosubstituted or disubstituted phenyl, phenoxy, benzyl, benzyloxy, naphthyl or naphthoxy group, the substituents being selected from linear or branched $(C_1-C_6)$ alkyl groups and $(C_1-C_6)$ alkoxy groups;

the β group, in which the $R_1$ and $R_2$ groups, together with the nitrogen atom, form a 3-membered to 10-membered, nitrogen-containing heterocyclic group, which may be unsubstituted or substituted with a linear or branched $(C_1-C_6)$ alkyl group, the nitrogen-containing heterocyclic group optionally containing one or more heteroatoms from selected from the group consisting of O, S or $NR^5$, the $R^5$ group being selected from a linear or branched $(C_1-C_6)$ alkyl group or a phenyl or benzyl group, unsubstituted, monosubstituted or disubstituted with linear or branched $(C_1-C_6)$ alkyl groups, the nitrogen-containing heterocyclic group being annelated with one or two benzene rings, or the χ group, in which the $R_1$ and $R_2$ groups, together with the nitrogen atom, form an azaadamantyl group;

$R_3$ and $R_4$ each independently are selected from hydrogen or a linear or branched $(C_1-C_6)$ alkyl group, a $(C_3-C_7)$ cycloalkyl group or a $(C_1-C_6)$ alkoxy group; or $R_1$ and $R_4$ or $R_2$ and $R_3$ together with the nitrogen atom form an $—R_2N—(CH_2)_k—X—$ or $—R_1N—(CH_2)_k—X—$ unit with one another, in which k=1 or 2 and which is linked to the benzene ring of a naphthopyran group, X being selected from O, S, $CH_2$, $C(CH_3)_2$, $C(C_6H_5)_2$, $N(CH_3)$ or $N(C_6H_5)$ and the $R_2$ or $R_1$ group then being selected from methyl or phenyl, a benzene ring optionally annelated to this $—R_2N—(CH_2)_k—X—$ or $—R_1N—(CH_2)_k—X—$ unit, or $NR_1R_2$, $R_3$ and $R_4$, together with the benzene ring of the naphthopyran group to which they are bound, form a julolidinyl unit;

B is selected from a julolidinyl group, bound over the 3 position to the pyran ring, a phenyl or naphthyl group, monosubstituted or disubstituted in the ortho or para position, the substituent or substituents being an $—NR_6R_7$ group, the $R_6$ and $R_7$ groups being selected independently of one another from a $(C_3-C_7)$ cycloalkyl group or a phenyl or benzyl group, substituted with one or more linear or branched $(C_1-C_6)$ alkyl groups or $(C_1-C_6)$ alkoxy groups, or the $R_6$ and $R_7$ groups, together with the nitrogen atom of the $—NR_6R_7$ group forming an azaadamantyl group or a 3- to 10-membered, nitrogen-containing heterocyclic group, which may be unsubstituted or substituted with a linear or branched $(C_1-C_6)$ alkyl group, the nitrogen-containing heterocyclic group containing one or more heteroatoms selected from the group consisting of O, S and $NR^5$ and optionally being annelated with one or two benzene rings, or two directly adjacent substituents at the phenyl or naphthyl group forming an $—R_8N—(CH_2)_k—X—$ group, in which k is 1 or 2, X being selected from O, S, $CH_2$, $C(CH_3)_2$, $C(C_6H_5)_2$, $N(CH_3)$ or $N(C_6H_5)$ and the $R_8$ then being selected from methyl or phenyl, with the proviso that the $—R_8N$ unit is linked in the ortho or para position, and B' is selected from a phenyl or naphtyl group, unsubstituted or monosubstituted, disubstituted or trisubstituted in the ortho or para position, the substituents being selected from a linear or branched $(C_1-C_6)$ alkyl group, a $(C_3-C_7)$ cycloalkyl group, a $(C_1-C_6)$ alkoxy group, fluorine, chlorine or bromine, the phenyl on naphthyl groups of the B and B' units being linked independently of one another directly via an ethylene group or an ethinediyl group (i.e., an acetylene group) to the 3,3'-position of the 3H-naphtho [2,1-b]-pyran system.

By introducing at least two amine functions in the 8 position of the naphthopyran group as well as at one of the geminal aryl groups in the 3 position of the naphthopyran group, the photochromic properties of 3H-naphtho[2,1-b]-pyrans can be markedly improved. 3H-naphtho[2,1-b]-pyrans are made available for the first time which, in comparison to corresponding compounds from the prior art, absorb at clearly longer wavelengths in the excited form. As a result, violet to blue photochromic dyes can be produced in only a few reaction steps. Moreover, the photochromic 3H-naphtho[2,1-b]-pyrans according to the invention exhibit a good service life and rapid brightening rates while, at the same time, maintaining a good darkening performance.

BRIEF DESCRIPTION OF THE DRAWINGS

The invention will be described in further detail hereinafter with reference to illustrative preferred embodiments.

DETAILED DESCRIPTION OF PREFERRED EMBODIMENTS

Figure 1:
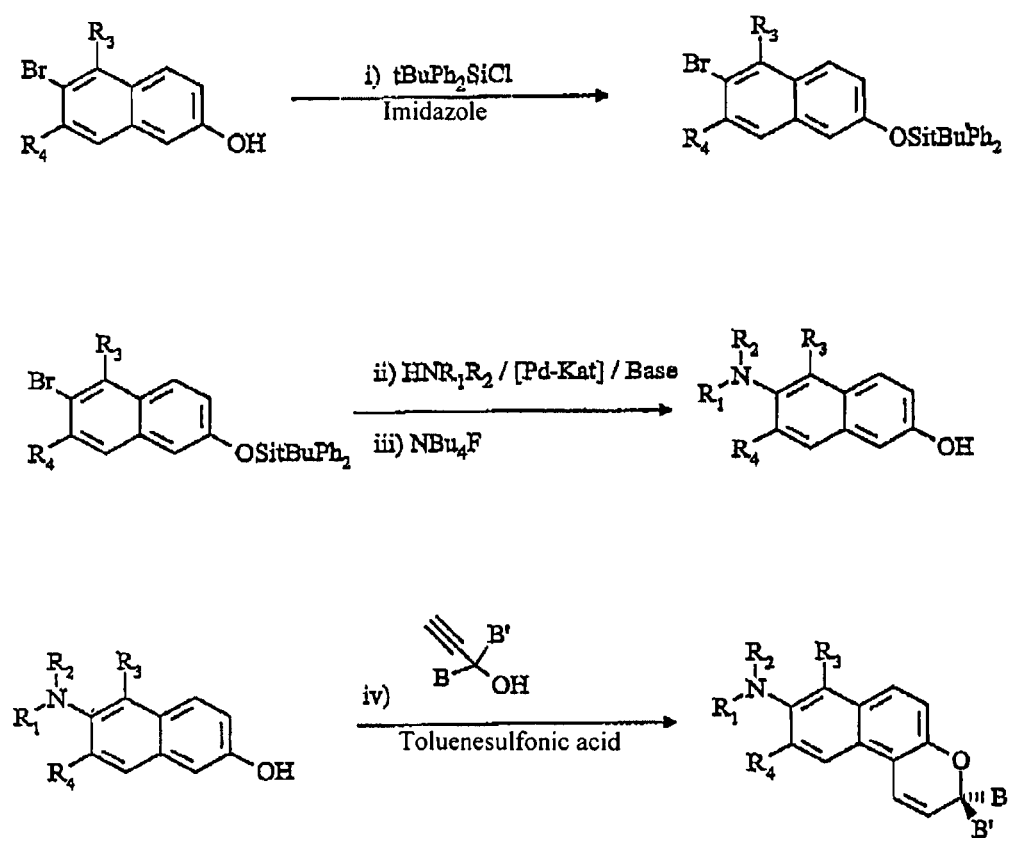
FIG. 1 depicts one example of a procedure for synthesizing representative examples of photochromic compounds in accordance with the present invention.

In one preferred embodiment of the present invention, $R_1$ and $R_2$ of the above Formula (I) are selected from the group consisting of phenyl, phenoxy, benzyl, benzyloxy, naphthyl and naphthoxy, which is unsubstituted, monosubstituted or disubstituted, or $R_1$ and $R_2$ together with the nitrogen atom form a 3- to 10-membered, nitrogen-containing heterocyclic group, especially a morpholine group, a thiomorpholine group, a piperidine group, an azacycloheptane, an azacyclooctane group, a 1,4-diaza-1-methyl-cycloheptane group, a piperazine group, an (N'-$(C_1-C_6$ alkyl)piperazine group, a pyrrolidine group, an imidazolidine group, a pyrazolidine group, an aziridine group, an azetidine group, an indoline group, a carbazole group, a phenothiazine group, a phenazine group, a phenoxazine group, a tetrahydroquinoline group and a tetrahydrosioquinoline group. More preferably, the $NR_1R_2$ group in the above Formula (I), as a whole, represents diphenylamino, dianisylamino, morpholinyl, thiomorpholinyl, 3,5-dimethylthiomorpholinyl, piperidinyl, azacyclo-heptyl, azacycloctyl, 1,4-diaza-1-methylcycloheptyl, piperazinyl, pyrrolidinyl or 1,2,3,4-tetrahydroisoquinolinyl.

When the $NR_1R_2$, $R_2$ and $R_4$ groups, together with the benzene ring of the naphthopyran group to which they are linked, form a julolidinyl unit, the following structural unit is obtained:

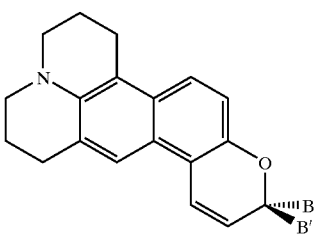

Julolidinyl Substitution

If the $R_1$ and $R_4$ or $R_2$ and $R_3$ groups, together with the nitrogen atom, respectively form a —$R_2$N—(CH$_2$)$_k$—X— or —$R_1$N—(CH$_2$)$_k$—X— unit, which is defined as above and is linked to the benzene ring of the naphthopyran group, then the following structural units are preferred:

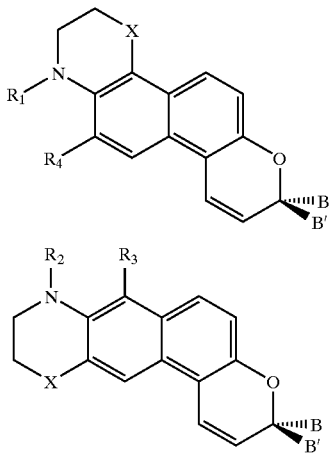

In the foregoing structural units, X is preferably selected from the group consisting of O, CH$_2$ and N(CH$_3$).

In a further preferred embodiment of the present invention, the B group preferably is selected from a phenyl group, which is substituted in the para position by an —NR$_6$R$_7$ group, the R$_6$ and R$_7$ groups together with the nitrogen atom of the —NR$_6$R$_7$ group forming an azaadamantyl group or a nitrogen-containing 3-membered to 10-membered heterocyclic group, especially a morpholine group, a thiomorpholine group, a piperidine group, an azacycloheptane group, an azacyclooctane group, a 1,4-diaza-1-methylcycloheptane group, a piperazine group, an N-(N'-(C$_1$-C$_6$ alkyl)piperazine group, a pyrrolidine group, or the phenyl group substituted in the para position by an —NR$_6$R$_7$ group represents as a whole an N-methyl-1,2,3,4-tetrahydroquinolinyl group, which is attached in the 6 position, so that the structural unit is as follows:

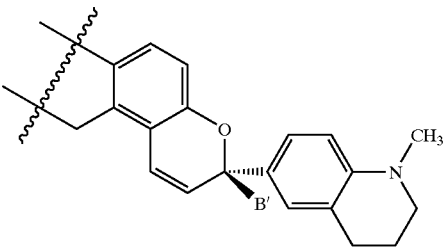

In yet another preferred embodiment, the B group preferably is a 4-dimethylaminophenyl group.

If the B group represents a julolidinyl group, which is attached via the 3 position to the pyran ring, the following structural unit is obtained:

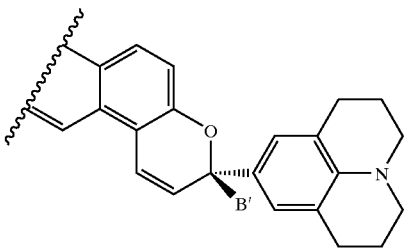

Especially preferred photochromic 3H-naphtho[2,1-b]-pyran compounds according to the present invention include:

(1) 8-(N-morpholinyl)-3-phenyl-3-(4-(N-pyrrolidinyl)phenyl)-3H-naphtho[2,1-b]pyran,
(2) 8-(N-morpholinyl)-3-phenyl-3-(4-(N-piperidinyl)phenyl)-3H-naphtho[2,1-b]pyran,
(3) 3-(4-(N-azacycloheptyl)phenyl)-8-(N-morpholinyl)-3-phenyl-3H-naphtho-[2,1-b]pyran,
(4) 3-(4-(N-azacyclooctyl)phenyl)-8-(N-morpholinyl)-3-phenyl-3H-naphtho-[2,1-b]pyran,
(5) 3-(4-(N-azacyclooctyl)phenyl)-8-(N-3,5-dimethylmorpholinyl)-3-phenyl-3H-naphtho-[2,1-b]pyran,
(6) 3-(4-(N-azacyclooctyl)phenyl)-3-phenyl-8-(N-thiomorpholinyl)-3H-naphtho-[2,1-b]pyran,
(7) 3-(4-(N-azacyclooctyl)phenyl)-3-phenyl-8-(N-pyrrolidinyl)-3H-naphtho-[2,1-b]pyran,
(8) 3-(4-((di-4-anisyl)amino)phenyl)-3-phenyl-8-(N-piperidinyl)-3H-naphtho-[2,1-b]pyran,
(9) 3-phenyl-8-(N-piperidinyl)-3-(4-(N-pyrrolidinyl)phenyl)-3H-naphtho-[2,1-b]pyran,
(10) 3-(6-(N-methyl-1,2,3,4-tetrahydrochinolinyl)-3-phenyl-8-(N-piperidinyl)-3H-naphtho-[2,1-b]pyran,
(11) 3-(4-(N-azacyclooctyl)phenyl)-3-phenyl-8-(N-piperidinyl)-3H-naphtho-[2,1-b]pyran,
(12) 3-(4-(1,4-diaza-1-methylcycloheptyl)phenyl)-8-(N-piperidinyl)-3-phenyl-3H-naphtho-[2,1-b]pyran,
(13) 3-(4-(N-azacyclooctyl)phenyl)-3-phenyl-8-(N-piperidinyl)-3H-naphtho-[2,1-b]pyran,
(14) 3-(4-(N-azacycloheptyl)phenyl)-3-phenyl-8-(N-1,2,3,4-tetrahydroisoquinolinyl)-3H-naphtho-[2,1-b]pyran,
(15) 3-(4-(N-morpholinyl)phenyl)-3-phenyl-8-(N-1,2,3,4-tetrahydroisoquinolinyl)-3H-naphtho-[2,1-b]pyran,
(16) 8-(N-azacycloheptyl)-3-(4-(N-morpholinyl)phenyl)-3-phenyl-3H-naphtho-[2,1-b]pyran,
(17) 3-(4-(N-azacycloheptyl)phenyl)-8-diphenylamino-3-phenyl-3H-naphtho-[2,1-b]pyran,

(18) 3-((4-dimethylamino)phenyl)-8-diphenylamino-3-phenyl-3H-naphtho-[2, 1-b]pyran,
(19) 3-((4-dimethylamino)phenyl)-8-diphenylamino-3-(2-fluorphenyl)-3H-naphtho-[2,1-b]pyran, and
(20) 3-dimethylamino-3-(4-diphenylamino)phenyl-3-phenyl-3H-naphtho-[2,1-b]pyran.

The longest wavelength absorption maxima of the open form of the foregoing examples of photochromic 3H-naphtho[2,1-b]-pyran compounds according to the present invention are listed in the following Table:

| Compound | Longest wavelength absorption maximum of the open (colored) form (measured in a methacrylate polymer) | Optical color impression |
| --- | --- | --- |
| (1) | 575 nm | blue violet |
| (2) | 555 nm | Violet |
| (3) | 580 nm | Blue |
| (4) | 575 nm | blue violet |
| (5) | 580 nm | Blue |
| (6) | 585 nm | Blue |
| (7) | 590 nm | Blue |
| (8) | 570 nm | blue violet |
| (9) | 580 nm | Blue |
| (10) | 580 nm | Blue |
| (11) | 585 nm | Blue |
| (12) | 570 nm | blue violet |
| (13) | 580 nm | Blue |
| (14) | 590 nm | Blue |
| (15) | 555 nm | Violet |
| (16) | 580 nm | Blue |
| (17) | 590 nm | Blue |
| (18) | 575 nm | blue violet |
| (19) | 575 nm | blue violet |
| (20) | 590 nm | Blue |

The compounds of the invention can be used in plastic materials or plastic objects of any shape or type for a plurality of purposes, for which the photochromic behavior is important. In this regard, a single dye according to the present invention or a mixture of such dyes can be used. For example, the photochromic 3H-naphtho[2,1-b]-pyran dyes of the invention can be used in lenses, especially in ophthalmic lenses, in lenses for spectacles of all types, such as ski goggles, sunglasses, motorcycle glasses, visors of protective helmets and the like. Furthermore, the photochromic benzo[f]chromic dyes can also be used, for example, as protection against the sun in vehicles and occupied rooms in the form of windows, protective shutters or shades, coverings, roofs or the like.

To produce such photochromic objects, the photochromic 3H-naphtho[2,1-b]-pyran dyes of the invention can be applied to or embedded within a polymer material, such as an organic synthetic resin, by various methods known in the art; for example, as described in WO 99/15518.

In this connection, a distinction is made between so-called bulk dyeing methods and surface dyeing methods. A bulk dyeing method comprises, for example, the dissolving or dispersing of the photochromic compound or compounds of the present invention in a synthetic resin material, for example, by the addition of the photochromic compound or compounds to a monomer material before the monomer is polymerized. Further possibilities for producing photochromic objects include, for example, the permeation of the plastic material or materials with the photochromic compound or compounds by immersing the plastic material in a hot solution of the photochromic dye of the present invention or a thermal transfer method. The photochromic compound or compounds can also be provided, for example, in the form of a separate layer between adjoining layers of the plastic material, for example, as part of a polymeric film. Furthermore, it is also possible to apply the photochromic compound or compounds as part of a coating on the surface of the plastic material. The expression "permeation" describes the migration of the photochromic compound or compounds into the plastic material, for example, via a solvent-assisted transfer of the photochromic compound or compounds into a polymer matrix, the vapor phase transfer or other such surface diffusion processes. Advantageously, photochromic objects, such as eyeglasses, can be produced not only by means of the usual bulk dyeing, but also, in the same manner, by means of surface dyeing. In the latter variation, a surprisingly slight tendency to migrate can be achieved. This is advantageous especially for the subsequent finishing steps, since layer detachments and similar defects are drastically reduced by the lesser back diffusion in vacuum, for example, during the application of an anti-reflection coating.

All in all, any coloring process based on the photochromic 3H-naphtho[2,1-b]-pyran dyes of the invention which is compatible from a chemical point of view and in terms of the color effect which is achieved, can be used to apply or embed the dyes of the invention in the synthetic resin in order to satisfy aesthetic considerations as well as medical and fashion aspects. The specifically selected dye or dyes can accordingly be varied independently of the intended effects and requirements.

The photochromic 3H-naphtho[2,1-b]-pyran dyes of the invention which correspond to the Formula (I) can be synthesized, for example, according to the reaction outline given in FIG. 1.

Starting out from suitably substituted 2-naphthols, the hydroxy group is initially protected in step I), preferably with a t-butyldiphenylsilyl ether protective group. Subsequently, in step II), a unit which contains an appropriate amine group is introduced in the 6 position of the resulting protected naphthol by a palladium-catalyzed amination. The leaving group in the 6 position of the naphthol may be a bromine or iodine atom or a Triflat group. After the silyl ether protective group is removed in step III), the resulting substituted 2-naphthol compounds are reacted with suitably substituted 2-propine-1-ol compounds in accordance with step iv) to yield the compounds of the invention.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A photochromic 3H-naphtho[2,1-b]-pyran compound corresponding to formula (I)

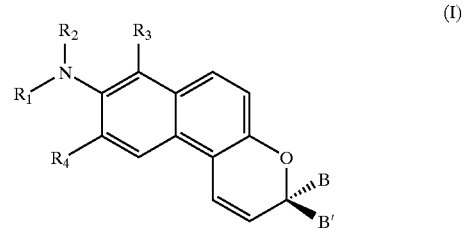

wherein
$R_1$ and $R_2$ are independently selected from:
a linear or branched ($C_1$–$C_6$) alkyl group, a ($C_3$–$C_7$) cycloalkyl group, and an unsubstituted, monosubstituted or disubstituted phenyl, phenoxy, benzyl, benzyloxy, naphthyl or naphthoxy group, wherein any substituents are selected from the group consisting of linear or branched ($C_1$–$C_6$) alkyl groups and ($C_1$–$C_6$) alkoxy groups, or $R_1$ and $R_2$ together with the nitrogen atom to which they are bound form a 3- 10-membered, nitrogen-containing heterocyclic group, which may be unsubstituted or substituted with a linear or branched ($C_1$–$C_6$) alkyl group, wherein the nitrogen-containing heterocyclic group optionally contains one or more heteroatoms selected from the group consisting of O, S and $NR^5$, wherein $R^5$ is a linear or branched ($C_1$–$C_6$) alkyl group or a phenyl or benzyl group, unsubstituted or monosubstituted or disubstituted with linear or branched ($C_1$–$C_6$) alkyl groups, said nitrogen-containing heterocyclic group being annelated with one or two benzene rings, or $R_1$ and $R_2$ together with the nitrogen atom to which they are bound form an azaadamantyl group;

$R_3$ and $R_4$ are independently selected from the group consisting of hydrogen, linear or branched ($C_1$–$C_6$) alkyl groups, ($C_3$–$C_7$) cycloalkyl groups, and ($C_1$–$C_6$) alkoxy groups, or $R_1$ and $R_4$ or $R_2$ and $R_3$ together with the nitrogen atom respectively form an —$R_2$N—$(CH_2)_k$—X— or —$R_1$N—$(CH_2)_k$—X— unit, in which k=1 or 2 and which is attached to the benzene ring of a naphthopyran group; wherein X is selected from the group consisting of O, S, $CH_2$, $C(CH_3)_2$, $C(C_6H_5)_2$, $N(CH_3)$ and $N(C_6H_5)$, and the remaining $R_2$ or $R_1$ group is selected from the group consisting of methyl, phenyl, and a benzene ring, optionally annelated to the —$R_2$N—$(CH_2)_k$—X— or —$R_1$N—$(CH_2)_k$—X— unit, or $NR_1R_2$, $R_3$ and $R_4$ together with the benzene ring of the naphthopyran group to which they are bound form a julolidinyl unit;

B is selected from the group consisting of a julolidinyl group bound via the 3 position to the pyran ring; a phenyl or naphthyl group, monosubstituted or disubstituted in the ortho or para position, the substituent or substituents being a —$NR_6R_7$ group, wherein $R_6$ and $R_7$ are independently selected from a ($C_3$–$C_7$) cycloalkyl group or a phenyl or benzyl group, substituted with one or more linear or branched ($C_1$–$C_6$) alkyl groups or ($C_1$–$C_6$) alkoxy groups, or wherein $R_6$ and $R_7$ together with the nitrogen atom to which they are bound form an azaadamantyl group or a 3- to 10-membered, nitrogen-containing heterocyclic group, which may be unsubstituted or substituted with a linear or branched ($C_1$–$C_6$) alkyl group, wherein said nitrogen-containing heterocyclic group contains one or more heteroatoms selected from the group consisting of O, S and $NR^5$ and optionally is annelated with one or two benzene rings; or wherein two directly adjacent substituents on said phenyl or naphthyl group form an —$R_8$N—$(CH_2)_k$—X— group, wherein k is 1 or 2; X is selected from the group consisting of O, S, $CH_2$, $C(CH_3)_2$, $C(C_6H_5)_2$, $N(CH_3)$ and $N(C_6H_5)$, and $R_8$ is methyl or phenyl, with the proviso that the —$R_8$N unit is attached in the ortho or para position; and B' is selected from the group consisting of phenyl and naphthyl, wherein said phenyl or naphthyl is unsubstituted or monosubstituted, disubstituted or trisubstituted in the ortho or para position with substituents selected from the group consisting of linear or branched ($C_1$–$C_6$) alkyl groups, ($C_3$–$C_7$) cycloalkyl groups, ($C_1$–$C_6$) alkoxy groups, fluorine, chlorine and bromine; and wherein the phenyl or naphthyl groups of B and B' may independently be attached directly, via an ethylene group or an ethinediyl group to the 3,3'-position of the 3H-naphtho[2,1-b]-pyran system.

2. A compound according to claim 1, wherein $R_1$ and $R_2$ are independently selected from the group consisting of phenyl, phenoxy, benzyl, benzyloxy, naphthyl, and naphthoxy and may be unsubstituted, monosubstituted or disubstituted, or $R_1$ and $R_2$ together with the nitrogen atom to which they are bound form a 3- to 10-membered nitrogen-containing heterocyclic group.

3. A compound according to claim 2, wherein $R_1$ and $R_2$ together with the nitrogen atom to which they are bound form a nitrogen-containing heterocyclic group selected from the group consisting of a morpholine group, a thiomorpholine group, a piperidine group, an azacycloheptane group, an azacyclooctane group, a 1,4-diaza-1-methyl-cycloheptane group, a piperazine group, an (N'-($C_1$–$C_6$ alkyl)piperazine group, a pyrrolidine group, an imidazolidine group, a pyrazolidine group, an aziridine group, an azetidine group, an indoline group, a carbazole group, a phenothiazine group, a phenazine group, a phenoxazine group, a tetrahydroquinoline group, and a tetrahydrosioquinoline group.

4. A compound according to claim 1, wherein the $NR_1R_2$ group in Formula (I) represents a diphenylamino, dianisylamino, morpholinyl, thiomorpholinyl, 3,5-dimethylthiomorpholinyl, piperidinyl, azacycloheptyl, azacyclooctyl, 1,4-diaza-1-methyl-cycloheptyl, piperazinyl, pyrrolidinyl or 1,2,3,4-tetrahydroisoquinolinyl group.

5. A compound according to claim 1, wherein B represents a phenyl group substituted in the para position by an —$NR_6R_7$ group, wherein $R_6$ and $R_7$ together with the nitrogen atom to which they are bound form an azaadamantyl group or a 3- to 10-membered nitrogen-containing heterocyclic group.

6. A compound according to claim 5, wherein B is a nitrogen-containing heterocyclic group selected from the group consisting of a morpholine group, a thiomorpholine group, a piperidine group, an azacycloheptane group, an azacyclooctane group, a 1,4-diaza-1-methylcycloheptane group, a piperazine group, an (N'-($C_1$-$C_6$ alkyl)piperazine group and a pyrrolidine group.

7. A compound according to claim 5, wherein B is an N-methyltetrahydro-quinolinyl group attached in the 6 position.

8. A 3H-naphtho[2,1-b]-pyran compound according to claim 1, selected from the group consisting of:

8-(N-morpholinyl)-3-phenyl-3-(4-(N-pyrrolidinyl)phenyl)-3H-naphtho [2,1-b]pyran;

8-(N-morpholinyl)-3-phenyl-3-(4-(N-piperidinyl)phenyl)-3H-naphtho [2,1-b]pyran;

3-(4-(N-azacycloheptyl)phenyl)-8-(N-morpholinyl)-3-phenyl-3H-naphtho-[2,1-b]pyran;

3-(4-(N-azacyclooctyl)phenyl)-8-(N-morpholinyl)-3-phenyl-3H-naphtho-[2,1-b]pyran;

3-(4-(N-azacyclooctyl)phenyl)-8-(N-3,5-dimethylmorpholinyl)-3-phenyl-3H-naphtho-[2,1-b]pyran;

3-(4-(N-azacyclooctyl)phenyl)-3-phenyl-8-(N-thiomorpholinyl)-3H-naphtho-[2,1-b]pyran;

3-(4-(N-azacyclooctyl)phenyl)-3-phenyl-8-(N-pyrrolidinyl)-3H-naphtho-[2,1-b]pyran;

3-(4-((di-4-anisyl)amino)phenyl)-3-phenyl-8-(N-piperidinyl)-3H-naphtho-[2,1-b]pyran;

3-phenyl-8-(N-piperidinyl)-3-(4-(N-pyrrolidinyl)phenyl)-3H-naphtho-[2,1-b]pyran;

3-(6-(N-methyl-1,2,3,4-tetrahydrochinolinyl)-3-phenyl-8-(N-piperidinyl)-3H-naphtho-[2,1-b]pyran;

3-(4-(N-azacyclooctyl)phenyl)-3-phenyl-8-(N-piperidinyl)-3H-naphtho-[2,1-b]pyran;

3-(4-(1,4-diaza-1-methylcycloheptyl)phenyl)-8-(N-piperidinyl)-3-phenyl-3H-naphtho-[2,1-b]pyran;

3-(4-(N-azacyclooctyl)phenyl)-3-phenyl-8-(N-piperidinyl)-3H-naphtho-[2,1-b]pyran;

3-(4-(N-azacycloheptyl)phenyl)-3-phenyl-8-(N-1,2,3,4-tetrahydroisoquinolinyl)-3H-naphtho-[2,1-b]pyran;

3-(4-(N-morpholinyl)phenyl)-3-phenyl-8-(N-1,2,3,4-tetrahydroisoquinolinyl)-3H-naphtho-[2,1-b]pyran;

8-(N-azacycloheptyl)-3-(4-(N-morpholinyl)phenyl)-3-phenyl-3H-naphtho-[2,1-b]pyran;

3-(4-(N-azacycloheptyl)phenyl)-8-diphenylamino-3-phenyl-3H-naphtho-[2,1-b]pyran;

3-((4-dimethylamino)phenyl)-8-diphenylamino-3-phenyl-3H-naphtho-[2,1-b]pyran;

3-((4-dimethylamino)phenyl)-8-diphenylamino-3-(2-fluorphenyl)-3H-naphtho-[2,1-b]pyran; and 3-dimethylamino-3-(4-diphenylamino)phenyl-3-phenyl-3H-naphtho-[2,1-b]pyran.

9. A photochromic article comprising a synthetic resin body and a photochromically effective amount of at least one compound according to claim 1, coated on or dispersed in said synthetic resin body.

10. An article according to claim 9, wherein said synthetic resin body is an ophthalmic lens.

* * * * *